(12) United States Patent
Contreras et al.

(10) Patent No.: US 10,279,304 B2
(45) Date of Patent: *May 7, 2019

(54) GAS CHROMATOGRAPHY TEMPERATURE MODULATION

(71) Applicant: PHILLIPS 66 COMPANY, Houston, TX (US)

(72) Inventors: Jesse A. Contreras, Bartlesville, OK (US); Mike R. Deal, Caney, KS (US); James L. Malandra, Tulsa, OK (US); Kenneth S. McGee, Ponca City, OK (US)

(73) Assignee: Phillips 66 Company, Houston, TX (US)

( * ) Notice: Subject to any disclaimer, the term of this patent is extended or adjusted under 35 U.S.C. 154(b) by 244 days.

This patent is subject to a terminal disclaimer.

(21) Appl. No.: 15/438,045

(22) Filed: Feb. 21, 2017

(65) Prior Publication Data
US 2017/0239608 A1 Aug. 24, 2017

Related U.S. Application Data

(60) Provisional application No. 62/299,098, filed on Feb. 24, 2016.

(51) Int. Cl.
*B01D 53/22* (2006.01)
*B01D 53/02* (2006.01)
*G01N 30/46* (2006.01)
*G01N 30/02* (2006.01)

(52) U.S. Cl.
CPC ......... *B01D 53/025* (2013.01); *G01N 30/465* (2013.01); *G01N 2030/025* (2013.01)

(58) Field of Classification Search
CPC ........... G01N 2030/025; G01N 30/465; B01D 53/025
See application file for complete search history.

(56) References Cited

U.S. PATENT DOCUMENTS

| | | | | | |
|---|---|---|---|---|---|
| 4,704,141 | A | * | 11/1987 | Krebber | G01N 30/24 73/23.41 |
| 5,318,729 | A | * | 6/1994 | Kurihara | G02F 1/3616 252/582 |
| 5,970,803 | A | * | 10/1999 | Staples | G01N 1/2214 73/23.41 |
| 6,354,160 | B1 | * | 3/2002 | Staples | G01N 1/2214 73/863.12 |
| 6,442,995 | B1 | * | 9/2002 | van der Maas | G01N 30/12 422/89 |
| 8,889,423 | B2 | * | 11/2014 | Oda | G01N 30/84 422/70 |
| 2002/0014106 | A1 | * | 2/2002 | Srinivasan | B01J 19/0046 73/23.42 |
| 2004/0082611 | A1 | * | 4/2004 | Kobayashi | C07D 207/08 514/317 |
| 2005/0048662 | A1 | * | 3/2005 | Cai | G01N 30/463 436/161 |

(Continued)

*Primary Examiner* — Anthony R Shumate
(74) *Attorney, Agent, or Firm* — Phillips 66 Company

(57) ABSTRACT

The present disclosure relates generally to processes for separating chemical compounds via two-dimensional gas chromatography. Certain embodiments comprise rapid heating and cooling of the second dimension column by a unique arrangement of heating and cooling elements.

18 Claims, 3 Drawing Sheets

(56) References Cited

U.S. PATENT DOCUMENTS

| | | | |
|---|---|---|---|
| 2007/0273882 A1* | 11/2007 | Smith | G01N 21/39 |
| | | | 356/437 |
| 2011/0283771 A1* | 11/2011 | Gerstel | G01N 30/10 |
| | | | 73/23.41 |
| 2015/0276689 A1* | 10/2015 | Watanabe | G01N 30/06 |
| | | | 422/89 |
| 2016/0193546 A1* | 7/2016 | Shimizu | B01J 20/26 |
| | | | 554/191 |
| 2017/0241960 A1* | 8/2017 | Contreras | G01N 30/30 |
| 2017/0358754 A1* | 12/2017 | Hayashi | C09K 11/06 |

* cited by examiner

GAS CHROMATOGRAPHY TEMPERATURE MODULATION

CROSS-REFERENCE TO RELATED APPLICATIONS

This application is a non-provisional application which according to 35 U.S.C. § 119(e), claims the benefit of, and the right of priority to, U.S. Provisional Application Ser. No. 62/299,098 filed Feb. 24, 2016, entitled "Gas Chromatography Temperature Modulation," both of which are incorporated herein in their entirety, as permitted under 37 CFR 1.57(b).

FIELD OF THE INVENTION

The present invention relates generally to a method and system for acquisition of seismic data in a marine environment. More particularly, but not by way of limitation, embodiments of the present invention include methods and systems for acquiring seismic data in a marine environment using survey paths following a series of linked deviated paths or linked curved paths.

BACKGROUND

The basic principles and the concept of two-dimension gas chromatography ((GC×GC)) have been well established. The modulator is considered as the key component of ((GC×GC)) supported by an appropriate choice of conditions and columns. Its main functions are to: 1) repeatedly accumulate or trap narrow "zones" of the effluent from the first dimension (1D) column; 2) refocus, and, 3) release the collected effluent into the second dimension (2D) column. Rapid sampling allows the original 1D column separation to be approximately preserved. The 2D column separation is optimally completed before the next release of a accumulated 1D column effluent in order to minimize wrap-around (i.e., the overlap of adjacent 1D effluent samples in the 2D column). This is typically achieved by performing the 2D column separation in just a few seconds (e.g., 2-12 sec). The time constraints on the 2D separation are not conducive to temperature gradients. Therefore the 2D column separation is generally limited to isothermal conditions.

The isothermal separation of complex samples by GC suffers from the general elution problem in which the first peaks are not fully-resolved and the later eluting peaks are spread and broad. As a result, typical (GC×GC) chromatograms do not take advantage of the entire second dimension space. A conventional solution to the general elution problem is programmed temperature gradient gas chromatography (PTGC). However, the application of PTGC in the second dimension is constrained due to the short analysis time available (<12 sec).

Accordingly, a need exists for better (GC×GC) systems and methods that allow rapid temperature cycling of the 2D column, thereby facilitating programmed temperature gradient gas chromatography (PTGC) in the 2D column and better separation of complex samples without causing wrap-around of 1D samples or necessitating the use of multiple second dimension columns.

BRIEF SUMMARY

Certain embodiments of the invention comprise a process for two-dimensional gas chromatography, comprising: a) separating a mixture comprising chemical compounds by passing the mixture in gaseous phase in the presence of a carrier gas through a first gas chromatography capillary column to produce a first effluent comprising separated chemical compounds that exits the first gas chromatography capillary column over a period of time; b) intermittently gathering an aliquot of the effluent from the first chromatography capillary column at different times; c) injecting each aliquot in sequential fashion into a second gas chromatography capillary column and passing each aliquot through the second gas chromatography capillary column in the presence of a second carrier gas, producing a second effluent comprising separated chemical compounds. The flow rate of the second carrier gas is greater than the first carrier gas and immediately after the injection, a heating element is moved into close conductive proximity to the second gas chromatography capillary column to initiate a temperature gradient in the second gas chromatography capillary column.

Immediately after the producing of a second effluent, the heating element is moved out of close conductive proximity to the second gas chromatography capillary column and a cooling element is moved into close conductive proximity to the second gas chromatography capillary column.

In certain embodiments, the heating element and the cooling element are connected to generally opposing end portions of a shaft comprising a low thermal mass material, and movement of the shaft alternatively places either the heating element or the cooling element into close conductive proximity to the second gas chromatography capillary column.

In certain embodiments, the heating element is connected to a first shaft and the cooling element is connected to a second shaft, and each shaft comprises a low thermal mass material and moves independently from the other. In these embodiments, movement of the first shaft places the heating element into close conductive proximity to the second gas chromatography capillary column, and movement of the second shaft moves the cooling element into close conductive proximity to the second gas chromatography capillary column.

In certain embodiments, the temperature gradient comprises maintaining the second gas chromatography capillary column at a first temperature in the range from 5° C. to 40° C. until the injecting, then heating at a rate of at least 100° C. per second during the passing of each sample comprising 1D eluted compounds to achieve a temperature in the range from 100° C. to 350° C., then cooled at a rate of at least 100° C. per minute after the producing until the temperature of the second gas chromatography capillary column is returned to the first temperature. In certain embodiments, the connector comprises a low-thermal mass material.

In certain embodiments, the heating element and the cooling element of the moveable element alternatively insert into a generally cylindrical orifice formed by the second gas chromatography capillary column. In these embodiments, the generally cylindrical orifice may additionally comprise a conductive cylindrical sleeve that serves as a thermally conductive interface between the second gas chromatography capillary column and alternately, the heating element or the cooling element. In these embodiments, the second gas chromatography capillary column optionally is coiled around the perimeter of the conductive cylindrical sleeve.

In certain embodiments, the heating element and the cooling element each comprise a high thermal mass material, and the first and second shaft each comprise a low thermal mass material.

In certain embodiments, the heating element is heated by induction heating, thermal conduction heating, resistive heating or combinations of these. The heating element may heat the second gas chromatography capillary column to cause a temperature gradient over time within the second gas chromatography capillary column. In certain embodiments, the cooling element is cooled by direct contact with a cooled gas, a cooled liquid, a cooled solid or combinations thereof.

In certain embodiments, each aliquot of 1D eluted compounds elutes from the second gas chromatography column in less than 60 sec, optionally less than 30 sec.

In certain embodiments, the heating element inserts inside of a first thermally-insulated container when the heating element is not in close conductive proximity to the second gas chromatography capillary column. In certain embodiments, the cooling element inserts inside of a second thermally insulated container when the heating element is not in close conductive proximity to the second gas chromatography capillary column.

In certain embodiments, the heating element is at least partly heated by the first thermally insulated container when the heating element inserts inside the first thermally insulated container. In certain embodiments, the cooling element is at least partly cooled by the second thermally-insulated container when the cooling element inserts inside the second thermally-insulated container.

BRIEF DESCRIPTION OF THE DRAWINGS

A more complete understanding of the present invention and benefits thereof may be acquired by referring to the follow description taken in conjunction with the accompanying drawings in which.

Figure 1:
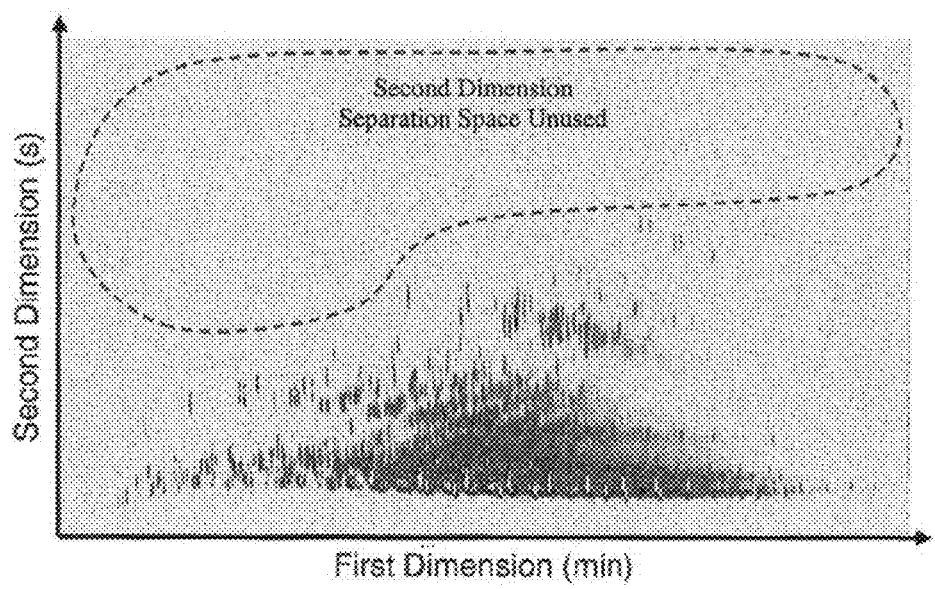
FIG. 1 depicts the results of a typical two-dimensional gas chromatography separation of various chemical compounds.

The invention is susceptible to various modifications and alternative forms, specific embodiments thereof are shown by way of example in the drawings. The drawings may not be to scale. It should be understood that the drawings and their accompanying detailed descriptions are not intended to limit the scope of the invention to the particular form disclosed, but rather, the intention is to cover all modifications, equivalents and alternatives falling within the spirit and scope of the present invention as defined by the appended claims.

DETAILED DESCRIPTION

In gas chromatography (GC), the variables that produce the greatest effects on separation efficiency and analysis time are the stationary phase, internal column diameter, operating column temperature, carrier gas, and carrier gas velocity. However, controlling the column temperature is the easiest and most effective way to influence the separation process. Currently, the two major operational modes in GC are isothermal GC (ITGC) and temperature programmed GC (TPGC). It is well-known that ITGC can produce higher resolution than TPGC; unfortunately, this advantage comes at the cost of prohibitively long analysis time that is effective only for relatively narrow volatility range of compounds. In TPGC, the column temperature increases at a given rate, allowing the analysis of mixtures with a wide range of molecular weights at the expense of some losses in separation power, especially when high heating rates are used.

In comprehensive two-dimensional gas chromatography (2D-GC), the sample is separated in two different columns connected in series. The separated sample from the 1D is collected in small fractions in a modulator, then each small fraction is successively transferred into the 2D column for a second independent separation. Because the separation taking place within the 1D does not stop, the size of each fraction collected in a modulator from the 1D and transferred to the 2D column is dependent on the speed of analysis in the 2D column. Thus, the 2D separation is typically achieved in few seconds (2 to 12). The goal is to complete the 2D separation for each fraction before the next fraction is introduced in the secondary column. This prevents overlap (or wraparound) of successive fractions at the detector that would destroy the separation achieved in the second dimension.

The required speed of separation in the second dimension decreases separation efficiencies because shorter second dimension columns are required in order to complete the analysis and to prevent wraparound. The total peak capacity of the (2D-GC) technique is greatly improved with the application of TPGC operation in the second dimension. However, the short analysis times required for the second dimension separation effectively prevent this. Conventional TPGC often utilizes resistive heating to achieve rapid heating rates, but cannot rapidly cool the entire second dimension column at a rate that allows injection of the next sample from the 1D in a suitable timeframe. Thus, the 2D column separation is typically conducted isothermally. Unfortunately, this limits the resolution of separation achieved in the 2D column and increases the general elution problem on the 2D (i.e., where the first peaks are not resolved and the later eluting peaks are spread and broad). As a result, the separation in the second dimension does not take advantage of the entire second dimension space, as can be seen in the conventional (GC×GC) chromatogram shown in FIG. 1.

However, even though fast TPGC separations have been achieved (<1 s), the long cooling times (~100 s) have limited its application in the second dimension of GC×GC separations.

High heating or cooling rates in GC are limited by the overall thermal mass of the GC system. The use of a low thermal mass (LTM) column holder assembly in combination with heating and cooling energy reservoirs and axial movement of the LTM column holder between the reservoirs is the key for achieving ballistic heating and cooling. Typical PTGC LTM systems, use resistive heating to perform fast heating rates but does not properly address the problem of slow cooling rates.

The present invention relates to novel systems and processes that improve resolution of compounds in the second dimension of (GC×GC), while minimizing the time required for separation in the 2D column. The separation of compounds provided by the combination of the two columns in series optimally results in an overall resolution that is a product of the individual column resolutions. This high resolution technique is ideal for the separation of complex mixtures such as crude oil and diesel and heavier refinery streams whose components are not well resolved by a single capillary GC column.

Certain embodiments comprise rapidly-cycling temperature gradient in the second dimension column that is facilitated by alternately placing the 2D column in close conductive proximity to either a heating element or a cooling element. In certain embodiments, the heating and cooling elements are connected via a low thermal mass connector, and axial movement of the connector places the second dimension GC column in close conductive proximity with either the heating or cooling element. The low thermal mass nature of the fused silica GC column used for the second dimension separation allows it to rapidly match the temperature of each reservoir when the column is placed within close conductive proximity.

Rapid cycling of the 2D column between the heating element and the cooling element enables rapid conductive heating of the 2D column to assist with increasing the resolution and separation of a broader range of compounds in a given fraction of sample eluted from the 1D column. This novel design greatly enhances the separation power and broadens the range of compounds that can be resolved (e.g., a sample of crude petroleum comprising compounds covering a broad range of boiling points).

The heating element may be heated by any known method of heating, including (but not limited to) exposure to combustion gases, microwave radiation, infrared heating, inductive heating and resistive-electrical heating. In certain embodiments, the heating reservoir is maintained at a temperature that is higher than the temperature of the GC oven. The temperature could follow the heating rate of the oven. The cooling element (such as, but not limited to a heat sink or cold reservoir) is maintained at a temperature of less than 0° C. The cooling element may be cooled with any cryogenic gas suitable for conductively removing heat from the cooling element, which in turn, conductively absorbs heat from the 2D column. In certain embodiments, this gas may be, $CO_2$ or $N_2$.

In certain embodiments, the heating element and cooling element are connected in a manner that allows the two elements to move in unison and that facilitates alternative placement of each element within close conductive proximity of the 2D column. In certain embodiments, the heating element and cooling element are connected by a low thermal mass (LTM) connector. Optionally, the LTM connector is rod-shaped and directly connects to the heating element at one end and the cooling element at the opposite end. This configuration allows simultaneous translational movement of both the heating element and cooling element in the same direction along a path that is parallel with the axis of the rod-shaped connector. This translational movement may be driven by attaching the connector to a motor or solenoid that is controlled to alternately place either the heating element or the cooling element in close conductive proximity to the 2D column. In certain embodiments, the movement of the LTM connector may be performed by directly attaching an electromagnetic drive or linear actuator, such as (but not limited to) a LinMot™ brand linear motor. The rapid movement of the linear motor quickly and precisely moves the LTM connector, which in turn places either the heating or cooling element in close conductive proximity to the 2D column. In certain embodiments, the heating element is placed in close conductive proximity to the 2D column to increase the temperature of the 2D column from a first temperature in the range from 0° C. to 40° C. to a second temperature that is in the range from 100° C. to 350° C. When the LTM connector is moved to alternately place the cooling element in close conductive proximity to the 2D column, the 2D column is rapidly cooled back to the first temperature.

In certain alternative embodiments, the heating element and the cooling element are not directly connected, and the movement of each is independently controlled by an independent motor or solenoid. In such embodiments, alternative placement of either the heating element or cooling element in close conductive proximity to the 2D column requires the operation of the two independent motors or solenoids to be orchestrated by a common control mechanism in order to prevent collision between the heating and cooling elements.

In other embodiments, the 2D column is heated resistively by a heating wire placed in close conductive proximity to the 2D column. Such embodiments lack a movable heating element, and after heating of the 2D column ceases, rapid cooling of the 2D column back to the first temperature is enabled by rapid movement of the cooling element into close conductive proximity of the 2D column.

Figure 2:
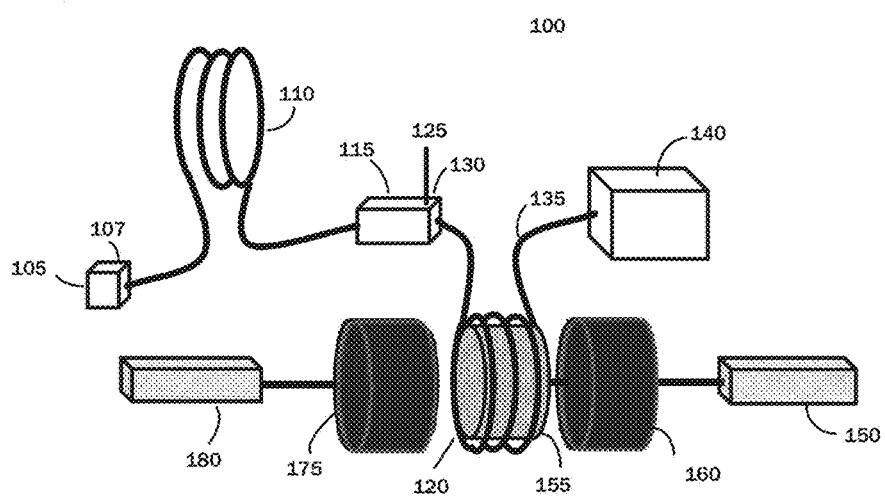
FIG. 2 is a simplified schematic of a two-dimensional gas chromatography system in accordance with an embodiment of the present disclosure.

FIG. 2 illustrates one embodiment of the system and method for a 2D gas chromatography system 100 employing a first dimension gas chromatography (1D) column 110 and a second dimension capillary gas chromatography (2D) column 120 connected in series and separated by a modulator 115. A sample 105 is placed into injector 107, which injects the sample into the 1D column 110 with the assistance of a pressurized first carrier gas (not depicted). The 1D column 110 is held at a constant temperature in the range from ° C. and the sample is subjected to chromatographic separation in the 1D column to produce a 1D effluent comprising separated compounds that accumulate in the modulator 115. The modulator 115 accumulates a fraction of the effluent for a set amount of time (that is optimized according to the chemical composition of the sample 105). After the set amount of time, the modulator 115 transfers (or re-injects) the fraction of the effluent into the 2D column 120. The modulator 115 then repeats the process, accumulating another fraction for the set amount of time for later injection onto the 2D column 120.

Modulators are conventional in nature and various types are known in the art, including (but not limited to) valves, Deans switches and thermal sweep arms. Optionally, the modulator 115 is a cryogenic modulator that cools each fraction of effluent accumulated from the 1D column to prevent a loss of peak resolution as the fraction awaits injection onto the 2D column. Modulator technology is conventional, and the type of modulator utilized is not not integral to the invention. Thus, modulators will not be in greater detail.

Again referring to the embodiment depicted in FIG. 2, the fraction of effluent is injected into the 2D column 120 by a second carrier gas (not depicted) that is pressurized and typically flows through the 2D column 120 in order to facilitate rapid separation of compounds in the 2D column. The second carrier gas flows at a faster rate than the first carrier gas utilized in the 1D column to allow the 2D separation to proceed rapidly and prevent wraparound of fractions of the effluent collected in the modulator 115. Optionally, the second carrier gas enters the 2D column via an inlet 130 to the modulator 115. Separated compounds 135 exiting the 2D column are passed to a detector 140 to obtain a series of short second dimension chromatograms that quantify the separated compounds.

In certain embodiments, the heating element and cooling element are not directly connected, and each element is moved by a separate motor or solenoid configured so that the heating element or the cooling element can be alternately moved to be in close conductive proximity to the 2D column. An exemplary embodiment of such an arrangement is presented in FIG. 2 and FIG. 3.

Again referring to FIG. 2, injection of each fraction of 1D effluent into the 2D column 120 is aided by a pressurized second carrier gas 125 that enters the modulator via an inlet 130 and carries each fraction of 1D effluent through the 2D column 20 where chemical compounds in the effluent are rapidly separated. The second carrier gas flows at a faster rate than the first carrier gas utilized in the 1D column to allow the 2D separation to proceed more rapidly, thereby preventing wraparound (i.e., overlap) of compounds accumulated in successive fractions of the 1D effluent collected in the modulator 115. Optionally, the second carrier gas 125 enters the 2D column 120 via an inlet 130 to the modulator 115. Separated compounds elute from the 2D column as 2D effluent that is conveyed to a detector 140 to obtain a series of short second dimension chromatograms that quantify the separated compounds.

Further referring to the embodiment depicted in FIG. 2, 2D column 120 is typically held at a first temperature in the range of 5° C. to 40° C. prior to injection of each fraction of 1D effluent. Immediately following injection of each fraction of 1D effluent into the 2D column 120, the temperature of 2D column 120 is rapidly increased to a second, higher temperature that is in the range from 100° C. to 350° C. This rapid increase in temperature of the 2D column coincides with placement of a heating element 155 into close conductive proximity to the 2D column 120. The temperature of heating element 555 is maintained at a constant temperature in the range of 300° C. to 600° C. that allows the rapid transfer of heat to the 2D column. The rapidly-increasing temperature gradient in the 2D column facilitates more efficient separation of compounds present in the 1D effluent injected from the modulator 115. These separated compounds elute from the 2D column 120, as a 2D effluent 135 that is conveyed to detector 440.

Once elution of each 2D effluent is completed (typically in 2-12 seconds), motor 150 retracts heating element 155 from close conductive proximity to the 2D column 120 and into a thermal sleeve 160 that may serve to insulate the heating element 155 and/or assist in heating the heating element 155 to a temperature in the range from 300° C. to 600° C. The system 100 further comprises a cooling element 170 that sits in a cooling element sleeve 175. Similar to the heating element, the cooling element 170 can be move in a linear fashion via a direct connection with motor 180.

Figure 3:
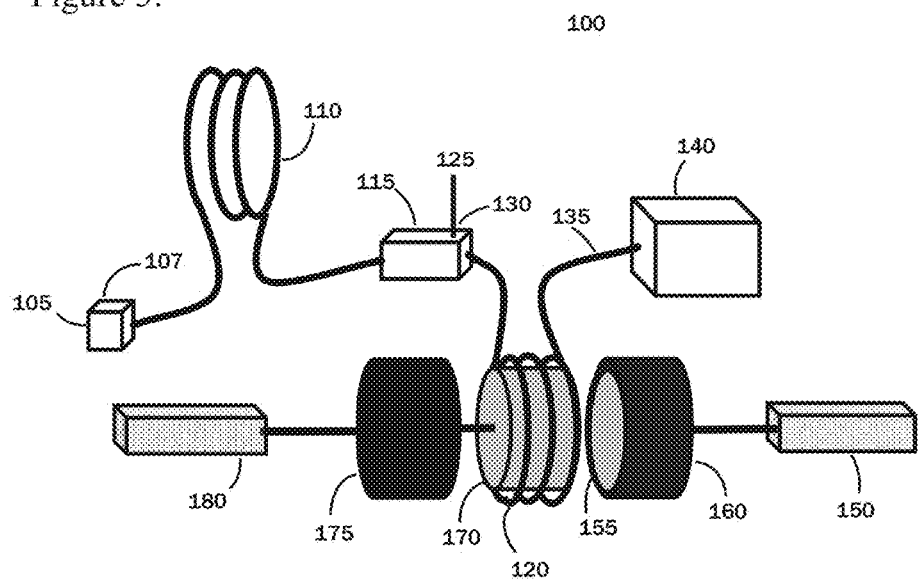
FIG. 3 is a simplified schematic of a two-dimensional gas chromatography system in accordance with an embodiment of the present disclosure.

FIG. 3 illustrates alternate linear movement of the heating element 155 and cooling element 170 to alternatively place each element in close conductive proximity to the 2D column 120. This arrangement facilitates rapid heating of the 2D column 120 to facilitate separation of compounds. Upon elution of the 2D effluent 135 (comprising separated compounds) to detector 140, a second motor 180 moves cooling element 170 out of close conductive proximity with cooling element sleeve 175 and into close conductive proximity with the 2D column 120 to rapidly cool the column back to a temperature in the range from 5° C. to 40° C. Cooling element sleeve 175 may serve to insulate the cooling element, or optionally assist in removing heat from cooling element 170. When the cooling element 170 is within the cooling element sleeve 175, the cooling element is held at a temperature in a range from 0° C. to −273° C., but in any event would be cooled to a temperature that allows rapid removal of heat from the 2D column, thereby returning the 2D column to a temperature ranging from 5° C. to 40° C. within a time of less than about 10 seconds, optionally less than about 6 seconds.

The detector 140 may comprise any of a number of different conventional GC detectors that are known in the art and are suitable for use with the present inventive systems and processes. The particular type of detector utilized is not critical and outside the scope of the invention. Thus, such detectors will not be discussed further here.

The use of conductive heat transfer with the heating element and cooling element facilitates rapid programmed heating and cooling of the 2D column, which enables PTGC in the second dimension. This unique systems and processes described herein greatly improve the utilization of the second dimension space, increasing separation efficiency by fixing the general elution problem currently existent in the second dimension. Furthermore, longer second dimension columns can be used, resulting in an overall increase in the peak capacity of the GC×GC system. This broadens the chemical species identification capabilities of the GC×GC methods for complex samples, such as crude oils and fractions thereof.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. Thus, the invention disclosed herein is specifically intended to be as broad as the claims below and those variations and equivalents that are encompassed by the scope of the claims. The abstract and drawings are not intended to limit the scope of the invention.

We claim:

1. A two-dimensional gas chromatography process, comprising the steps of:
   separating a mixture comprising chemical compounds by passing the mixture in gaseous phase in the presence of a carrier gas through a first gas chromatography capillary column to produce a first effluent comprising separated chemical compounds that exits the first gas chromatography capillary column over a period of time;
   (a) intermittently gathering an aliquot of the effluent from the first chromatography capillary column at different times;
   (b) injecting each aliquot in sequential fashion into a second gas chromatography capillary column and passing each aliquot through the second gas chromatography capillary column in the presence of a second carrier gas, thereby producing a second effluent comprising separated chemical compounds,
   wherein the flow rate of the second carrier gas is greater than the first carrier gas,
   wherein immediately after the injection, a heating element is moved into close conductive proximity to the second gas chromatography capillary column to initiate a temperature gradient in the second gas chromatography capillary column,
   wherein immediately after the producing of a second effluent, the heating element is moved out of close conductive proximity to the second gas chromatography capillary column and a cooling element is moved into close conductive proximity to the second gas chromatography capillary column.

2. The process of claim 1, wherein the heating element and the cooling element both are connected to generally opposing end portions of a shaft, wherein movement of the shaft alternatively places either the heating element or the cooling element into close conductive proximity to the second gas chromatography capillary column.

3. The process of claim 1, wherein the heating element is connected to a first shaft and the cooling element is connected to a second shaft, wherein each shaft comprises a low thermal mass material-and moves independently from the other and movement of the first shaft places the heating element into close conductive proximity to the second gas chromatography capillary column, and wherein movement of the second shaft moves the cooling element into close conductive proximity to the second gas chromatography capillary column.

4. A process according to claim 1, wherein the temperature gradient comprises maintaining the second gas chromatography capillary column at a first temperature in the range from 10° C. to 100° C. until the injecting, then heating at a rate of at least 100° c. per second during the passing of each sample to achieve a temperature in the range from 100, then cooled at a rate of at least 100° c. after the producing until the temperature of the second gas chromatography capillary column is returned to the first temperature.

5. A process according to claim 2, wherein the shaft comprises a low-thermal mass material.

6. A process according to claim 1, wherein the heating element and the cooling element alternatively insert into a generally cylindrical orifice formed by the second gas chromatography capillary column.

7. A process according to claim 6, wherein the generally cylindrical orifice additionally comprises a conductive cylindrical sleeve that serves as a thermally conductive interface between the second gas chromatography capillary column and alternately, the heating element or the cooling element.

8. A process according to claim 7, wherein the second gas chromatography capillary column is coiled around a perimeter of the conductive cylindrical sleeve.

9. A process according to claim 3, wherein the heating element and the cooling element each comprise a high thermal mass material.

10. A process according to claim 1, wherein the heating element is heated by induction heating, thermal conduction heating, resistive heating or combinations thereof.

11. A process according to claim 1, wherein the heating element heats the second gas chromatography capillary column to cause a temperature gradient over time within the second gas chromatography capillary column.

12. A process according to claim 1, wherein the cooling element is cooled by direct contact with a cooled gas, a cooled liquid, a cooled solid or combinations thereof.

13. A process according to claim 1, wherein each aliquot elutes from the second gas chromatography column in less than 60 seconds.

14. A process according to claim 1, wherein each aliquot elutes from the second gas chromatography column in less than 30 seconds.

15. A process according to claim 1, wherein the heating element inserts inside of a first thermally insulated container when the heating element is not in close conductive proximity to the second gas chromatography capillary column.

16. A process according to claim 1, wherein the cooling element inserts inside of a second thermally insulated container when the heating element is not in close conductive proximity to the second gas chromatography capillary column.

17. The process according to claim 15, wherein the heating element is at least partly heated by the first thermally insulated container when the heating element inserts inside the first thermally insulated container.

18. The process according to claim 16, wherein the cooling element is at least partly cooled by the second thermally-insulated container when the cooling element inserts inside the second thermally-insulated container.

* * * * *